United States Patent [19]

Hirsch

[11] Patent Number: 4,514,361

[45] Date of Patent: Apr. 30, 1985

[54] STEAM STERILIZATION INDICATOR

[75] Inventor: Arthur Hirsch, Elizabeth, N.J.

[73] Assignee: Arvey Corporation, Chicago, Ill.

[21] Appl. No.: 423,242

[22] Filed: Sep. 24, 1982

[51] Int. Cl.³ .................. A61L 2/06; G01N 21/80; G01N 31/22

[52] U.S. Cl. .................. 422/26; 422/56; 422/57; 422/119; 436/1

[58] Field of Search ............... 422/26, 56, 57; 436/1

[56] References Cited

U.S. PATENT DOCUMENTS

| | | | |
|---|---|---|---|
| 3,000,706 | 9/1961 | Royce | 436/1 |
| 3,346,464 | 10/1967 | Ernst | 436/1 X |
| 3,360,338 | 12/1967 | Edenbaum | 422/57 |
| 3,704,096 | 11/1972 | Verses et al. | 436/1 |
| 3,862,824 | 1/1975 | Chapman | 422/56 |
| 4,410,493 | 10/1983 | Joslyn | 422/56 X |

Primary Examiner—Michael S. Marcus
Assistant Examiner—Brion P. Heaney
Attorney, Agent, or Firm—Dressler, Goldsmith, Shore, Sutker & Milnamow, Ltd.

[57] ABSTRACT

A steam sterilization indicator including a carrier, a pH value indicator that changes color at a predetermined pH value affixed to the carrier and a chemical composition associated with the carrier. The chemical composition contains a mixture of at least two different carboxyl group-containing submixtures, wherein the first carboxyl group containing submixture is a mixture of 2,4-dihydroxybenzoic acid and a metal salt of 2,4-dihydroxybenzoic acid, and the second carboxyl group containing submixture is a mixture of phenylpropiolic acid and a metal salt of phenylpropiolic acid, wherein the molar ratio of the first submixture to the second submixture is about 1:4 to 4:1. Under steam sterilization conditions, the pH value of the chemical composition exceeds the predetermined pH value, causing the pH value indicator to change color and indicate that sterilization is complete.

9 Claims, No Drawings

STEAM STERILIZATION INDICATOR

DESCRIPTION

1. Technical Field

The present invention relates to indicators that visually show that steam sterilization has been completed, and more particularly to such indicators that exhibit improved sensitivity to the time, temperature and steam exposure at which steam sterilization is completed.

2. Background Art

A biological equivalency chemical indicator requires a chemical reaction, the rate of which is controlled by a time-temperature-steam exposure relation that is equivalent to that of the thermal death rate of a biological substrate such as *Bacillus stearothermophilus* spores. The chemical reaction should preferably be capable of providing a visual showing that the reaction is over and sterilization has been completed.

Several patents have dealt with indicators for noting the completion of steam sterilization. Included among those patents are U.S. Pat. No. 4,121,714, No. 3,568,627, No. 3,386,807, No. 3,360,339, No. 3,360,338, No. 3,360,337 and No. 2,826,073 and No. 2,798,885.

U.S. Pat. No. 3,862,824 to Chapman discloses a steam sterilization indicator that includes a carrier and a pH value indicator deposited on the carrier. Also deposited on the carrier is a mixture of a carboxylic acid that loses carbon dioxide under steam sterilizing conditions together with a salt of that acid, which on exposure to steam produces alkali and causes a continuous change in pH value in the alkaline direction as exposure to steam continues. The pH value indicator changes color as the pH value changes to indicate the extent of exposure to steam that has occurred.

The indicators of U.S. Pat. No. 3,862,824 operate to indicate completion of steam sterilization. However, those indicators lack the desired sensitivity of an indicator that is used in a hospital environment where it is of great importance that the time-temperature-steam exposure relation produce a visual change that is constant and reproducible from indicator to indicator, and accurately notes when sterilization is completed.

For example, in a steam sterilization using partially neutralized 2,4-dihydroxybenzoic acid, the compound of the sole example of that patent, and bromcresol purple as pH value indicator, a color change occured at a time when sterilization was complete, but in some instances the color change reversed. In addition, relatively small changes in concentration of the acid and its salt were found to upset the timing of the color change.

Thus, the indicator of U.S. Pat. No. 3,862,824 was found to need improvement. One such improvement is described in the detailed description of the invention that follows.

SUMMARY OF THE INVENTION

The present invention relates to a steam sterilization indicator. This indicator includes a carrier, usually made of paper, and a pH value indicator that is affixed to the carrier. The pH indicator exhibits a change in color when a predetermined pH value is exceeded. A chemical composition, preferably acidic, is also associated with the carrier as by absorption, adsorption or deposition. The pH value of the chemical composition increases under steam sterilizing conditions to exceed the predetermined pH value at which the pH value color indicator changes color to thereby provide a visual means to show that sterilization is complete.

The chemical composition associated with the carrier contains a mixture of at least two different carboxyl group-containing compounds. The first of those mixed compounds is a member selected from the group consisting of a first carboxylic acid that loses carbon dioxide under steam sterilizing conditions, a salt of that first carboxylic acid that produces alkali under steam sterilizing conditions, and mixtures thereof. The second compound of the mixture is a member selected from the group consisting of a second carboxylic acid that loses carbon dioxide under steam sterilizing conditions, a salt of the second carboxylic acid that produces alkali under steam sterilizing conditions, and mixtures thereof. In particularly preferred practice, the first carboxylic acid is 2,4-dihydroxybenzoic acid while the second carboxylic acid is phenylpropiolic acid. The cation of the salt of the first and second carboxylic acids is preferably an alkali metal such as sodium or potassium cations.

A method of sterilizing articles using an indicator of this invention is also disclosed. According to this method, an indicator of this invention is supplied, placed into a steam sterilization apparatus along with an article to be sterilized and the apparatus is closed. Pressurized steam is supplied to the closed apparatus with the supply being maintained until the color of the pH indicator changes, thereby indicating that the predetermined pH value has been exceeded and that the article has been sterilized.

DETAILED DESCRIPTION OF THE INVENTION

The present invention is concerned with an indicator for steam sterilization systems that indicates sterilization to be complete under time-temperature-steam exposure conditions that are equivalent to those conditions which kill a biological substrate that is usually used for determining that sterilization is complete. One such biological substrate is spores of *Bacillus stearothermophilus* which are more resistant to heat than are all known pathogenic bacteria. *Stearothermophilus* spores are killed after exposure to pressurized steam in a hospital-type sterilizer for three minutes at a temperature of 270° F. (about 132° C.) or exposure for more than 12 minutes at a temperature of 250° F. (about 121° C.).

In using a biological indicator strip, the spore-containing strip is placed in an autoclave along with the articles to be sterilized. After completion of the sterilization cycle, the biological indicator is sent to a laboratory for analysis while the supposedly sterilized articles should be quarantined, awaiting the laboratory results. In the laboratory, the spore strips are placed in a nutrient broth and incubated for forty-eight hours to determine whether any spores survived the sterilization procedure.

In frequent practice, the hospital has neither the space for proper quarantining of the supposedly sterilized articles, nor a sufficient number of the articles themselves to permit actual quarantining. As a result, the supposedly sterilized articles are placed back into stock on the assumption that sterilization was proper and will be confirmed by a subsequent report from the laboratory.

A chemical indicator system that visually demonstrates completion of sterilization is beneficial for several reasons. First, use of a biological substrate is time consuming and expensive because once the sterilizer has been run for the time and at the temperature thought sufficient for sterilization to be complete, the biological substrate must be placed on a culture medium and incubated to allow the organisms to grow to determine whether the sterilization was successful. Second, a chemical reaction that visually demonstrates completion of sterilization can require no more time to use than that required by the sterilization itself. Third, the chemical indicator utilizes a positive result, color change, for its showing of sterilization, while the biological substrate procedure requires a negative result, no growth, to show that sterilization occurred. Negative results are usually considered to be poor proofs.

The present chemical indicator provides a means for determining that sterilization is complete by a low cost, rapid detection system whose results are known by the end of a sterilization cycle. This indicator can also provide a positive result that can be accurately and reproducibly correlated to the results obtained under the same sterilization conditions from a higher cost, slower biological indicator.

A chemical indicator of this invention that shows sterilization to be complete upon exposure to substantially the same steam sterilizing conditions e.g. pressurized steam, which kill sufficient *Bacillus stearothermophilus* spores to demonstrate sterilization of a biological indicator containing those spores has been completed is called a bioequivalent indicator. Preferably, a bioequivalent indicator requires about 20 to about 50 percent longer to change color under steam sterilizing conditions than is required to kill *Bacillus stearothermophilus* spores, using BIER/Steam Vessel test conditions that are discussed in Example 4.

The added time under BIER/Steam Vessel conditions typically amounts to about one minute, and provides an added margin of safety which is small compared to the typical 48 hours required to check a biological indicator. In actual hospital use conditions, a biological indicator and a bioequivalent, chemical indicator typically require the same amount of sterilization time because of the added times at elevated temperatures in the presence of steam that are involved in hospital sterilization.

The chemical indicator of this invention includes a carrier, having an affixed pH value indicator and an associated chemical composition. The indicator of this invention utilizes moisture and elevated temperature supplied by pressurized steam to effect the change in color that signifies that sterilization is completed.

The carrier is preferably a web of paper. Carrier webs made from synthetic fibers that accept and retain the pH value indicator and chemical composition are also useful. When large scale preparations of indicators are undertaken, each lot of carrier should exhibit a constant pH value when immersed in distilled or deionized water so that the predetermined pH value at which sterilization is completed will not be substantially affected by pH value differences between different lots of carrier. It is also preferred that the carrier be substantially ashless when burned so that it will contribute substantially no buffering capacity to the indicator system through the ions that would constitute an ash on burning. Most preferably, the carrier additionally exhibits a neutral pH value, i.e., about 6.5 to about 7.5, when immersed in distilled or deionized water.

Carriers that typically meet the above criteria are papers used in the chemical arts as filter or chromatography papers. An example of one such paper is that designated S&S #597 manufactured by Schleicher & Schuell, Inc. of Keene, N.H.

The pH value indicators useful herein include a wide variety of well known materials of varying chemical structures. These materials are also known as acid-base indicators.

The pH value indicators show a change in pH value by a change in color. The change in color can be from one color to another color such as blue to red or from colorless to a color such as red. A change from a color to colorless such as yellow to colorless is also encompassed within the phrase "change in color" as used herein.

The chemical compositions of this invention are preferably initially acidic and become more alkaline during steam sterilization. Thus, pH value indicators that change color above about pH 4 and below about pH 7.5 are preferred. More preferably, the pH value indicator changes color in the range of about pH 5 to about pH 7. Bromcresol purple, which changes from yellow to blue-purple in the pH value range of 5.2–6.8, is one of the more preferred indicators useful herein. A bioequivalent indicator changes color upon exposure of the indicator to the same steam sterilizing conditions of time, temperature and steam pressure which kill sufficient *Bacillus stearothermophilus* spores of a biological indicator to demonstrate that sterilization of the biological indicator has been completed.

It is to be noted that mixtures of pH value indicators can be used herein as well as single compounds. In addition, the selection of which pH value indicator or indicators to use is a function of the chemical composition utilized and the time-temperature-steam exposure relation for that composition. The selection of the particular pH value indicator is a relatively easy task for one skilled in the art once the components of the chemical composition, its initial pH value and the pH value after completion of steam sterilization are selected and determined.

The pH value indicator and chemical composition are affixed to and associated with the carrier, respectively. As used herein, the words "affixed" and "associated" in their various grammatical forms are meant to include attachment of the pH value indicator and chemical composition to the carrier by chemical bonding, adsorption, absorption, deposition on a surface of the carrier, and the like. In preferred practice herein, the carrier is dipped into a solution containing both the pH value indicator and chemical composition and then dried to provide affixation and association of the pH value indicator and chemical composition, respectively, to and with the carrier.

The chemical composition of this invention is a mixture of two carboxyl group-containing compounds. At the initiation of steam sterilization, and in the presence of the elevated temperature and moisture so introduced, the chemical composition exhibits a first pH value. By the time that steam sterilization is completed, the pH value of the chemical composition has increased to the point that pH value exceeds the predetermined pH value at which the color of the pH value indicator changes.

In other words, the initial pH value of the chemical composition is relatively more acidic (lower) than is the pH value of the composition during steam sterilization and when steam sterilization is completed. Thus, by proper selection of the ingredients of the chemical composition and the pH value indicator, the color of the indicator can be made to change by the increased pH value (alkalinity) of the composition and thereby show visually that sterilization is complete.

In preferred practice, the pH value of the chemical composition is initially acidic, i.e. the chemical composition is preferably acidic prior to the onset of sterilization. When steam sterilization is complete, the pH value of the composition is preferably near neutral. It is noted that a pH value change from acid to near neutral is only a preferred change, and that a change in pH value from acid to less acid, from the acidic side of neutral to the basic side of neutral, from slightly basic to more basic, and the like are also useful changes. The important feature of the change in pH value is that the pH value becomes more alkaline during the steam sterilizing process, and is more alkaline than the initial pH value when steam sterilization has been completed.

A desired change in pH value under steam sterilizing conditions can be achieved as described in U.S. Pat. No. 3,862,824. However, as noted before, use of the mixture of a single acid and the salt of the single acid that is described in that patent provides an indicator that is not as sensitive and reproducibly accurate as might be desired. On the other hand, the chemical composition of this invention provides an indicator that provides the desired sensitivity and reproducible accuracy.

The present chemical composition is a mixture of at least two different carboxyl group-containing compounds. The first compound of the mixture is selected from the group consisting of a first carboxylic acid that loses carbon dioxide under steam sterilizing conditions, a salt of that first carboxylic acid which itself produces alkali under steam sterilizing conditions, and mixtures thereof. The second compound of the mixture is selected from the group consisting of a second carboxylic acid that loses carbon dioxide under steam sterilizing conditions, a salt of the second carboxylic acid that produces alkali under steam sterilizing conditions, and mixtures thereof.

Several carboxylic acids and their salts are well known to decompose under steam sterilizing conditions. When the acids of this invention decompose, they form or release carbon dioxide. When the salts of those acids decompose, a carbonate or bicarbonate salt is formed, thereby producing a carbonate or bicarbonate salt; i.e., alkali.

Examples of carboxyl group-containing compounds useful herein, as represented by their carboxylic acid forms, include, but are not limited to, 2,4-dihydroxybenzoic acid, 2,6-dihydroxybenzoic acid, nitroacetic acid, acetoacetic acid, alpha, alpha-dimethylacetoacetic acid, phenylpropiolic acid, trihaloacetic acids such as trichloroacetic acid, 2,4,6-trinitrobenzoic acid, and the like. Mixtures of 2,4-dihydroxybenzoic acid and phenylpropiolic acid and their salts are particularly preferred herein as the two carboxyl group-containing submixtures used in the mixture of the chemical composition.

Salts of carboxylic acids useful herein include the metal salts such as calcium, copper, zinc, and the like. In preferred practice, an alkali metal salt such as a sodium, potassium or lithium salt is used as the metal salt of the carboxylic acid.

The two carboxyl group-containing compounds are present in the indicator in a molar ratio of about 10:1 to about 1:10. More preferably, the carboxyl group-containing compounds are present at a molar ratio of about 4:1 to about 1:4. 2,4-Dihydroxybenzoic acid and phenylpropiolic acid and their respective salts are most preferably present at a molar ratio of about 4:1 to about 1:2, in the order listed.

The carboxyl group-containing compounds preferably comprise about 5 to about 20 weight percent of the solution utilized for preparing the indicator by dipping the carrier. More preferably, the mixed carboxyl group-containing compounds comprise about 10 to about 15 weight percent of the solution. The percentages of carboxyl group-containing compounds are calculated as total solids, including the salt forms of the carboxyl group-containing compounds. Put differently, the solution utilized for dipping the carrier preferably contains about 400 to about 1800 millimoles of the carboxyl group-containing compounds per liter of solution, and more preferably about 300 to about 1200 millimoles per liter.

The ratio of total moles of carboxylic acid initially present in the chemical composition of the indicator relative to the total moles of carboxylic acid salt initially present calculated from the ingredients of the chemical composition is preferably at about 1:1 to about 1:30. More preferably, the molar ratio of total carboxylic acid to total carboxylic acid salt initially present in the indicator is about 1:2 to about 1:20.

It was surprising that a mixture of two carboxyl group-containing compounds would provide a more sensitive and more accurate indicator than does use of a single acid and its salt. The observed result was unexpected because in usual acid-base phenomena, a mixture of two acids or bases generally produces a broader titration end point than does a single compound. It was therefore thought that the use of a mixture of two carboxyl group-containing compounds might lessen the sensitivity and accuracy of the system rather than improving both since the chemical reactions leading to the observed color change involve neutralization as does a titration.

A satisfactory explanation for the improved sensitivity and accuracy of the present indicators has not been found.

Protection from the provision of false positive and false negative indications of the sterilization process is provided by the indicators of the present invention, so long as the indicators remain uncontaminated. Protection from contamination can be provided to the indicators by enclosure within an envelope that is substantially impervious to penetration of liquids and gases under ambient conditions, but permeable to both liquids and gases under the conditions of steam sterilization. Enclosure of the indicator also provides protection to the objects being sterilized from possible bleeding of the pH value indicator and/or one or more components of the chemical composition.

A polypropylene film sold under the trademark Extrell 11 by Exxon Chemicals America, Film Division of Houston, Tex., provides a suitable protecting envelope for the indicators of this invention. This polymer film can be heat sealed around the indicator, and is sufficiently transparent when used at a thickness of about 1 to about 3 mils to permit visual inspection of the indicator color.

A typical indicator can be manufactured by preparing a solution of the mixed carboxyl group-containing compounds and pH value indicator in a suitable solvent such as water or a mixture of water and a low boiling water-miscible solvent such as ethanol. The carrier is then dipped into the solution to affix the pH value indicator and associate the chemical composition to and with the carrier. The thereby impregnated carrier is then dried, cut to size and enveloped in the protective film, if such a film is used.

The components of the chemical composition can be admixed into the solution in the acid and acid salt forms that are ultimately utilized in preparing the indicator. More preferably, the acid form of each of the mixed carboxyl group-containing compounds is added to the solution, and a desired amount of base such as sodium hydroxide is added to prepare the desired quantities of acid and base forms that are utilized in the solution into which the carrier is dipped.

The indicator so manufactured can then be used by placing it in a steam sterilizing apparatus along with the article to be sterilized. The sterilizing apparatus is then closed and pressurized steam is supplied thereto to provide the requisite steam and elevated temperature. The supply of pressurized steam is maintained into the sterilizing apparatus until the color of the pH value indicator changes, thereby indicating that the predetermined pH value has been exceeded, and that sterilization is complete.

The present invention is further illustrated by the examples that follow.

Best Mode For Carrying Out The Invention

EXAMPLE 1

Indicators Containing a Single Carboxyl Compound

Indicators were prepared using S&S #597 paper manufactured by Schleicher & Schnell, Inc. Keene, N.H., as carrier. The carrier was dipped into a solution of Formula A or Formula B, below, dried and then subjected to steam sterilization in a hospital-type sterilizer as is discussed further below.

| Ingredient | Formula A* | Formula B* |
| --- | --- | --- |
| 2,4-Dihydroxybenzoic acid | 5 g (0.0300 m) | — |
| Phenylpropiolic acid | — | 5 g (0.0340 m) |
| Sodium hydroxide (1 normal, aqueous) | 18.75 ml | 29.5 ml |
| Bromcresol purple (2.5% in ethanol) | 5 ml | 4 ml |
| Water, distilled | 2 ml | — |
| Ethanol (95%) | Q.S. to 50 ml | Q.S. to 50 ml |

*As used in these and the following formulations: g = grams, m = moles and ml = milliliters.

Use of the indicator prepared from Formula A in an autoclave model 1250 LABCLAVE Steam Sterilizer manufactured by Sybron/Corporation of Rochester, N.Y., at steam pressures of 15 and 27 pounds per square inch at temperatures of 250° F. and 270° F., respectively, produced color changes from yellow to blue-purple in less than 18 minutes and less than 3 minutes, respectively. However, the indicator reverted to a yellowish shade when stored for about 24 hours at ambient conditions.

The use of additional amounts of 2,4-dihydroxybenzoic acid with the same amount of sodium hydroxide (Modified Formula A) changed the timing of the color change away from the above, desired, times. Times for the changes to occur at temperatures of each 250° F. and 270° F. are shown below in the Table for indicators from Modified Formula A.

| | Modified Formula A | |
| --- | --- | --- |
| Grams of | Time for Color Change (minutes) | |
| *DBA | 250° F. | 270° F. |
| 3.6 | less than 10 | less than 1 |
| 4.7 | less than 15 | less than 2 |
| 5.0 | less than 18 | less than 3 |

*DBA = 2,4-dihydroxybenzoic acid.

The indicator prepared from Formula B provided a color change that was too rapid. That indicator changed color in less than 1 minute at 270° F.

Indicators prepared using the same amount of phenylpropiolic acid as in Formula B, but with 21 ml and 28 ml of 1 normal sodium hydroxide changed color too slowly. Thus, at 250° F. the indicators so prepared changed color at more than 18 minutes, while at 270° F. they changed color at 10 and 3 minutes, respectively.

These results illustrate that steam sterilization chemical indicators that utilize one carboxyl group-containing compound can be prepared. However, these results also illustrate the lack of sensitivity, time control and accuracy as well as reversibility that such indicators possess.

EXAMPLE 2

Indicator Containing Mixed Carboxyl Compounds

An indicator of this invention was prepared using the carrier and method described in Example 1, and the chemical composition of Formula C that comprised a mixture of two different compounds that contain a carboxyl group. The ingredients of Formula C were as follows:

| | Formula C | |
| --- | --- | --- |
| Ingredient | | Amount |
| Phenylpropiolic acid | | 2.5 g (0.017 m) |
| 2,4-dihydroxybenzoic acid | | 2.5 g (0.015 m) |
| Sodium hydroxide (1 normal, aqueous) | | 24.0 ml |
| Bromcresol purple (2.5% in ethanol) | | 5 ml |
| Ethanol (95%) | | to 50 ml |

*Abbreviations are as discussed in Example 1.

Indicators prepared from Formula C were placed into hospital-type steam sterilizers using sterilizing temperatures of 250° F. and 270° F., respectively. At 250° F., the indicator was yellow at 18 minutes and showed a sharp change to blue-purple at 19 minutes. At 270° F., there was no color change at 2 minutes, and the desired yellow to blue-purple change occured after 3 minutes.

The above noted color changes with time at each of the two sterilizing temperatures were reproducible for the indicators so prepared, thereby illustrating the superior reproducibility of the present indicators. The indicators of this Example did not revert in color after their steam-initiated reaction.

EXAMPLE 3

Indicators Containing Mixed Carboxyl Compounds and Varied Amounts of Neutralization A series of four indicators of this invention were prepared using the carrier and method of Example 1, and contained the chemical compositions and pH value indicators of Formulas D, E, F and G. A constant mole ratio of the two carboxyl compounds was utilized for these indicators along with varied amounts of sodium hydroxide to change the mole ratio of acid to acid salt initially present in the compositions. The ingredients of Formulas D–G were as follows:

| Ingredient | Amounts in Formula* | | | |
|---|---|---|---|---|
| | D | E | F | G |
| 2,4-Dihydroxybenzoic acid | 3.75 g (0.023 m) | 3.75 g (0.023 m) | 3.75 g (0.023 m) | 3.75 g (.023 m) |
| Phenylpropiolic acid | 1.25 g (0.009 m) | 1.25 g (0.009 m) | 1.25 g (0.009 m) | 1.25 g (0.009 m) |
| Sodium hydroxide (1 normal aqeuous) | 15 ml | 20 ml | 25 ml | 30 ml |
| Bromcresol purple (2.5% in ethanol) | 5 ml | 5 ml | 5 ml | 5 ml |
| Ethanol (95%) | to 50 ml | to 50 ml | to 50 ml | to 50 ml |
| Calculated free acid | 0.017 m | 0.012 m | 0.007 m | 0.002 m |

*Abbreviations are as discussed in Example 1.

When subjected to hospital-type steam sterilization conditions, indicators prepared from Formulas D–G maintained the same sharp color change from yellow at 2 minutes to blue-purple after 3 minutes at 270° F. At 250° F., the times for the above color change occured at 15, 12, 12, and 6 minutes, respectively for Formulas D–G. These results illustrate the fine tuning and sensitivity of the color change of the indicators of this invention that can be achieved by progressively altering the amount of neutralization of the carboxylic acids in the chemical composition.

EXAMPLE 4

Bioequivalency Comparison

Twenty indicator strips of this invention (Indicator A) and same number commercially available chemical indicator strips (Indicator B) were compared for their ability to show equivalency to the sterilization results of an equal number of commercially available biological indicator strips that contained *Bacillus stearothermophilus* spores (Indicator C). The strips were run through heated cycles in a Biological Indicator Evaluator Resistometer (BIER) vessel in the absence and presence of steam. The BIER/Steam Vessel met the standards of the Association for the Advancement of Medical Instrumentation that were approved Mar. 27, 1981.

The BIER/Steam Vessel achieved sterilization conditions within 9±1 seconds of starting, controlled temperature to ±0.5° C. and permitted withdrawal of the contents within less than about 30 seconds. There is typically an appreciable time lag between start-up and attainment of sterilization temperature in a hospital-type sterilizer, and another time lag between completion of sterilization and removal of the sterilized article. In a typical hospital environment, there is therefore an uncontrolled, relatively long period of time during which the article to be sterilized is exposed to elevated temperature, pressure and steam near those values used for sterilization. While the typical hospital-type sterilizer controls time and temperature closely during sterilization, the rate at which the sterilizer reaches the desired sterilization conditions will depend upon its temperature from prior use or disuse.

The Table below, illustrates that indicator strips of this invention were equivalent to the biological indicator under dry heat conditions, while the commercially available chemical strip incorrectly showed sterilization. The Table also illustrates a margin of safety designed into the particular strip of this invention to permit no color change in the presence of steam of any strip at 250° F. and 7.0 minutes, and of 270° F. and 2.5 minutes, even though all of the biological indicator strips later showed no activity at those times and temperatures. These results illustrate the bioequivalency of the strips of the present invention.

TABLE

| | Comparative Indications of Sterility[1] | | |
|---|---|---|---|
| | Chemical Indicators (Percent changing color) | | Biological Indicator (Percent with live spores) |
| Time (Min.) | Indicator A[2] | Indicator B[3] | Indicator C[4] |
| | | 270° F. DRY | |
| 30 | 0 | 100 | 100 |
| | | 250° F. DRY | |
| 60 | 0 | 100 | 100 |
| | | 270° F. + STEAM | |
| 2.5 | 0 | 100 | 0 |
| 3.5 | 100 | 100 | 0 |
| | | 260° F. + STEAM | |
| 5.5 | 100 | 100 | 0 |
| | | 250° F. + STEAM | |
| 7.0 | 0 | 100 | 0 |
| 8.5 | 100 | 100 | 0 |

[1] The percentage values for the chemical indicators reflect percentage of strips that changed color to indicate sterilization, while the percentages for the biological indicator reflect the percentage of strips that had live, culturable spores. Consequently, 0% for the chemical indicators correlates to 100% for the biological indicator, and 100% for the chemical indicator correlates to 0% for the biological indicator.
[2] A chemical indicator of this invention prepared substantially identically to that of Example 3, using Formula F.
[3] A commercially available chemical indicator strip.
[4] A commercially available biological indicator strip containing spores of *Bacillus stearothermophilus*.

The present invention has been described with respect to preferred embodiments. It will be clear to those skilled in that art that modifications and/or variations of the disclosed compositions and methods can be made without departing from the scope of the invention set forth herein. The invention is defined by the claims that follow.

It is claimed:

1. A steam sterilization indicator comprising a carrier, a pH value indicator that exhibits a change in color when a predetermined pH value is exceeded affixed to said carrier, and a chemical composition associated with said carrier, the pH value of said chemical composition increasing under steam sterilizing conditions from an initial pH value to exceed said predetermined pH value,
    said chemical composition containing a mixture including at least a first and a second carboxyl group-containing submixture, wherein said first carboxyl group-containing submixture is a mixture of 2,4-dihydroxybenzoic acid and a metal salt of 2,4-dihydroxybenzoic acid, and said second carboxyl group-containing submixture is a mixture of phenylpropiolic acid and a metal salt of phenylpropiolic acid, and the mole ratio of said first carboxyl group-containing submixture to said second carboxyl group-containing submixture is about 1:4 to about 4:1.

2. A steam sterilization indicator comprising a carrier, a pH value indicator that exhibits a change in color at a pH value of about 5.8 to about 6.2 affixed to said carrier and an acidic chemical composition associated with said carrier, the pH value of said acidic chemical composition increasing under steam sterilizing conditions to exceed a pH value of about 5.8 to about 6.2, said acidic chemical composition containing a mixture of a first and a second carboxyl group-containing submixture, said mixture including 2,4-dihydroxybenzoic acid and a salt of 2,4-dihydroxybenzoic acid as the first of said submixtures, and phenylpropiolic acid and a salt of phenylpropiolic acid as the second of said submixtures, the molar ratio of said first and second carboxyl group-containing submixtures to each other being about 1:4 to about 4:1.

3. The steam sterilization indicator according to claim 2 wherein the molar ratio of said first carboxyl group-containing submixture to said second carboxyl group-containing submixture is about 4:1 to about 1:2.

4. The steam sterilization indicator according to claim 2 wherein said carrier is paper.

5. The steam sterilization indicator according to claim 2 wherein said chemical composition initially contains a mole ratio of total carboxylic acid to total carboxylic acid salt of about 1:1 to about 1:30.

6. The steam sterilization indicator according to claim 2 wherein said chemical composition initially contains a mole ratio of total carboxylic acid to total carboxylic acid salt of about 1:2 to about 1:20.

7. A method for indicating that an article has been sterilized by steam comprising the steps of:
supplying the steam sterilization indicator of claim 2;
placing said indicator into a steam sterilizing apparatus along with an article to be sterilized and closing said apparatus;
supplying pressurized steam into the closed sterilizing apparatus; and
maintaining said supply of pressurized steam into said closed sterilizing apparatus until the color of the pH value indicator changes, thereby indicating that the pH value of said composition exceeds about 5.8 to about 6.2, and that said article has been sterilized.

8. A bioequivalent steam sterilization indicator comprising a carrier, a pH value indicator that exhibits a change in color at a pH value of about 5.8 to about 6.2 affixed to said carrier and an acidic chemical composition associated with said carrier, the pH value of said acidic chemical composition increasing to exceed a pH value of about 5.8 to about 6.2 upon exposure of said indicator to the same steam sterilization conditions which kill sufficient *Bacillus stearothermophilus* spores to indicate steam sterilization to be completed for a biological indicator containing said spores, said acidic chemical composition containing a mixture of a first and a second carboxyl group-containing submixture, said mixture including 2,4-dihydroxybenzoic acid and a salt of 2,4-dihydroxybenzoic acid as the first of said submixtures, and phenylpropiolic acid and a salt of phenylpropiolic acid as the second of said submixtures, the molar ratio of said first and second carboxyl group-containing submixtures to each other being about 1:4 to about 4:1.

9. A method for indicating that an article has been sterilized by steam comprising the steps of:
supplying the bioequivalent steam sterilization indicator of claim 8;
placing said indicator into a steam sterilizing apparatus along with an article to be sterilized and closing said apparatus;
supplying pressurized steam into the closed sterilizing apparatus; and
maintaining said supply of pressurized steam into said closed sterilizing apparatus to provide substantially the same exposure of said indicator to said pressurized steam that kills sufficient *Bacillus stearotheomophilus* spores to demonstrate sterilization of a biological indicator containing said spores.

* * * * *